United States Patent
Grimm et al.

(10) Patent No.: US 9,351,498 B2
(45) Date of Patent: May 31, 2016

(54) DEVICE AND METHOD FOR NON-CONTACT IDENTIFYING OF RED TISSUE STRUCTURES AND ASSEMBLY FOR REMOVING A STRIP OF RED TISSUE STRUCTURES

(71) Applicant: Nordischer Maschinenbau Rud. Baader GmbH + Co. KG, Lübeck (DE)

(72) Inventors: Oliver Grimm, Schwerin (DE); Björn Rünger, Lübeck (DE); Arne Irmler, Lübeck (DE)

(73) Assignee: Nordischer Maschinenbau Rud. Baader GmbH + Co. KG, Lubeck (DE)

( * ) Notice: Subject to any disclaimer, the term of this patent is extended or adjusted under 35 U.S.C. 154(b) by 0 days.

(21) Appl. No.: 14/760,826

(22) PCT Filed: Jan. 14, 2014

(86) PCT No.: PCT/EP2014/050589
§ 371 (c)(1),
(2) Date: Jul. 14, 2015

(87) PCT Pub. No.: WO2014/111375
PCT Pub. Date: Jul. 24, 2014

(65) Prior Publication Data
US 2015/0342202 A1  Dec. 3, 2015

(30) Foreign Application Priority Data
Jan. 15, 2013  (EP) .................................... 13151359

(51) Int. Cl.
*A22C 17/00* (2006.01)
*A22C 25/18* (2006.01)
(Continued)

(52) U.S. Cl.
CPC .............. *A22C 17/008* (2013.01); *A22C 21/003* (2013.01); *A22C 25/04* (2013.01);
(Continued)

(58) Field of Classification Search
CPC ..... A22C 17/00; A22C 17/0073; A22C 17/08
USPC .................. 452/149, 150, 156–158
See application file for complete search history.

(56) References Cited

U.S. PATENT DOCUMENTS 3,800,363 A    4/1974 Lapeyre
RE33,917 E  *  5/1992 Lapeyre ................. A22C 25/00
                                                452/157
(Continued)

FOREIGN PATENT DOCUMENTS

DE   102008013525 A1   9/2009
WO       89/12397 A1  12/1989
WO    2008/016309 A1   2/2008

OTHER PUBLICATIONS

International Search Report dated Apr. 22, 2014 from International Patent Application No. PCT/EP2014/050589 filed Jan. 14, 2014.
(Continued)

*Primary Examiner* — Richard Price, Jr.
(74) *Attorney, Agent, or Firm* — Sunstone IP

(57) ABSTRACT

The present invention concerns an apparatus and a corresponding method for non-contact identifying of red tissue structures in products of slaughtered animal bodies, comprising a conveying device for continuous conveyance of the products in a conveying direction, a light source configured to generate a flat light field which is designed and adapted to form a light line running transversely to the conveying direction of the product from the flat light field, a detecting device for identifying the red tissue structures, which comprises at least one optical sensor for recording the portions of light reflected by the product, wherein the light source is configured as an infrared light source and the light source is arranged such that the plane of the flat light field relative to the conveying direction is tilted by a light field angle of less than 90°. The invention also concerns an arrangement for removal of a strip of red tissue structures from products of slaughtered animal bodies, comprising the apparatus for non-contact identifying of red tissue structures, a cutting device for partial or complete removal of the red tissue structures from the products, and a control device (both of the latter not shown) designed and adapted to control the cutting device along the regions determined by the apparatus for non-contact identifying of the red tissue structures.

15 Claims, 2 Drawing Sheets

(51) Int. Cl.
  *A22C 21/00* (2006.01)
  *G01B 11/25* (2006.01)
  *G01N 33/12* (2006.01)
  *G01N 21/3563* (2014.01)
  *A22C 25/04* (2006.01)
  *G01N 21/84* (2006.01)

(52) U.S. Cl.
  CPC ............ *A22C 25/18* (2013.01); *G01B 11/2518* (2013.01); *G01N 21/3563* (2013.01); *G01N 21/84* (2013.01); *G01N 33/12* (2013.01); *G01N 2021/845* (2013.01); *G01N 2201/06113* (2013.01)

(56) References Cited

U.S. PATENT DOCUMENTS

| | | | |
|---|---|---|---|
| 5,241,365 A | 8/1993 | Haagensen | |
| 7,452,266 B2 * | 11/2008 | Bottemiller | A22C 7/00 452/150 |
| 7,547,247 B2 * | 6/2009 | Schimitzek | A22B 5/007 452/157 |
| 7,841,264 B2 * | 11/2010 | Kim | B26D 3/10 452/156 |
| 7,918,718 B2 * | 4/2011 | Christensen | A22B 5/007 452/157 |
| 8,147,299 B2 * | 4/2012 | McKenna | A22B 5/007 452/155 |
| 8,339,596 B2 | 12/2012 | Sivertsen et al. | |
| 2011/0013181 A1 | 1/2011 | Sivertsen et al. | |

OTHER PUBLICATIONS

European Search Report dated Aug. 13, 2013 from European Patent Application No. 13151359.0 filed Jan. 15, 2013.

* cited by examiner

DEVICE AND METHOD FOR NON-CONTACT IDENTIFYING OF RED TISSUE STRUCTURES AND ASSEMBLY FOR REMOVING A STRIP OF RED TISSUE STRUCTURES

BACKGROUND

The present invention concerns an apparatus for non-contact identifying of red tissue structures in products of slaughtered animal bodies. Furthermore, the present invention concerns a method for non-contact identifying of red tissue structures in products of slaughtered animal bodies, and an arrangement for removing a strip of red tissue structures from products of slaughtered animal bodies.

Such apparatuses, methods and assemblies are used in various sectors of industrial processing of slaughtered animal bodies, for example in processing of fish, meat or poultry products, in particular in processing of fish fillets, for example in processing of tuna fish e.g. skipjack. The red tissue structures are usually heavily blooded tissue types which visually stand out from other tissues. For example said red tissue structures include heavily blooded muscle flesh.

It is known to illuminate the products to be examined, for example fish fillets, and detect the reflected partial radiation or the light radiation scattered in the product, in particular in a translucent product, by means of a detecting device in order to draw conclusions on the product composition. An apparatus and a method for contactless identification of characteristics of translucent products is described for example in document DE 10 2008 013 525 B4.

With the known apparatuses and methods it is indeed possible to detect foreign bodies and/or foreign tissue types, but there is no differentiation between different tissue types, so that the known apparatuses and methods are not suitable for identifying specific tissue types, in particular for identifying heavily blooded tissues.

SUMMARY

It is therefore the object of the present invention to propose an apparatus which allows a reliable identification and differentiation of differently blooded tissue types in the products. Furthermore, the object is to propose a corresponding method. The object is furthermore to propose an arrangement which reliably guarantees the automatic removal of certain tissue types from the products.

This object is achieved by an apparatus of the type cited hereinbefore, wherein the apparatus comprises a conveying device for continuous conveyance of the products in a conveying direction, a light source which is configured to generate a flat light field and is designed and adapted to form a light line running transversely to the conveying direction of the product from the flat light field, a detecting device for identifying the red tissue structures which comprises at least one optical sensor means for recording the portions of light reflected from the product, wherein the light source is designed as an infrared light source and the light source is arranged such that the plane of the flat light field is tilted relative to the conveying direction by a light field angle of less than 90°. The infrared light used is absorbed in the product more strongly in the areas of the red tissue structures than in the other tissue constituents of the product. The difference is particularly great between the red tissue structures and the other tissues, so that the areas with the red tissue structures are identified precisely and with high reliability. The present invention is therefore suitable in principle for identifying red tissue structures, for example heavily blooded tissues, in particular red muscle flesh. It is also possible to distinguish damaged tissue areas, for example bruised areas, from other tissue structures or product areas.

A further expedient embodiment of the invention is characterised in that the light source and the optical sensor means are arranged spaced apart in the conveying direction. Owing to the resulting arrangement of the light source and optical sensor means relative to the product, it is possible also to detect a height profile or height contour of the product.

According to a further advantageous embodiment of the invention, the detecting device is arranged such that the portions of light reflected by the product are absorbed at a viewing angle of less than 90° from the conveying direction. This offers the advantage that the light line running transversely to the conveying direction on the product is not partially shadowed by the surface unevenness of the product. Thus the light line is detected by the detecting device without gaps or interruptions and largely independently of unevenness on the product surface.

A preferred embodiment of the invention is characterised in that the light source and the detecting device are arranged such that the light field angle is greater than the viewing angle. This offers the advantage that the reflected portions of light which are absorbed by the detecting device at the viewing angle cannot be shadowed or concealed by unevenness on the surface of the product, so that the reflected portions of light in all cases reach the detecting device unobstructed.

A further preferred embodiment of the invention proposes that the detecting device is arranged downstream of the light source in the conveying direction. This arrangement also guarantees that the light line on the product is formed from the flat light field continuously and independently of surface unevenness.

According to a further preferred embodiment, the light source is configured as a linear laser. The linear laser has the advantage that the product is on the one hand exposed to light of high intensity so that the light penetrates correspondingly far into the product. This allows identification or distinction of lower-lying tissue structures, for example muscle flesh regions. On the other hand, the light from the linear laser is strongly focussed so that the light line is configured as narrowly as possible on the product. In other words, with the linear laser, a strong focussing of the light beam is achieved in as narrow a flat light field as possible, so that the light line hits the product with a high intensity and strongly focussed. This offers the advantage of high local resolution in the identification of red tissue structures and a very good sensitivity in distinction between the red tissue structures and other tissue types and/or further constituents of the product.

A further expedient embodiment of the invention is characterised in that the light source has a wavelength between 600 nm and 1200 nm. Further preferably, the light source has a wavelength between 650 nm and 900 nm. Light with a wavelength between 650 nm and 900 nm is absorbed strongly because of the particularly pronounced absorption properties of the red tissue structures, so that the portions of light scattered into the product or reflected are attenuated relatively greatly. For this reason, the line width analysed by a detecting device on the product in the areas of red tissue structures has a significantly smaller width than in other areas, since the strong attenuation of the light beam in the red tissue structures reduces the light scatter range correspondingly greatly. In the other areas in which the absorption of the incident light beam is significantly less, the scatter range is significantly greater so that the line width of the light line in these areas is correspondingly wider. On the basis of the different line widths, a reliable and precise identification of red tissue structures is possible.

According to a further preferred embodiment of the invention, the detecting device is designed and adapted for receiving a plurality of individual images. In other words, the detecting device is configured and designed for cyclic recording of a plurality of images of the product or the light line present on the product. In this way, the course of the contour of the product is detected so that the position of the red tissue structures is determined over the entire product length.

A further expedient embodiment of the invention is characterised in that the detecting device comprises an analysis means which is designed and adapted to determine border lines between areas of red tissue structures and the other product areas of the product on the basis of the individual images. This offers the advantage that a detecting device is designed and adapted to determine the borders between the red tissue structures and the other areas. The border lines may for example serve as cut lines for subsequent processing of the product.

According to a further advantageous embodiment of the invention, the analysis means for determining lines of the same light intensity in the individual images is designed and adapted to determine the border lines. The light lines or line courses of the same light intensity, known as isolux, thus form the starting basis for determining the border lines. In this way it furthermore possible, by specifying a light intensity threshold value, to adjust variably the region delimited by the border lines around the red tissue structures. The light intensity threshold value serves to predefine the position or distance from the red tissue structures at which the border lines are detected or determined. In other words, a tolerance range can be set to guarantee that no constituents of the red tissue structures are present outside the region marked by the border lines in the product.

Furthermore, the object is achieved by an arrangement of the type cited hereinbefore, wherein the arrangement comprises an apparatus for non-contact identifying of red tissue structures in the products, a cutting device for partial or complete removal of the red tissue structures from the products, a control device which is adapted and designed to control the cutting device along the regions determined by means of the apparatus for non-contact identifying of red tissue structures, wherein the apparatus for non-contact identifying of red tissue structures in the products is configured according to any one of claims 1 to 10. By means of the arrangement according to the invention, it is possible for the first time to remove the red tissue structures from the products fully automatically, reliably and precisely.

According to a further preferred embodiment, the cutting device is configured moveably relative to the product. This offers the advantage that during the passage of one of the continuously conveyed products, the cutting device can be brought to the product or into the product in order to adapt the cut guidance precisely to the area of the determined red tissue structures or border lines.

A further expedient embodiment of the invention is characterised in that the cutting device comprises at least one actuator by means of which the cutting device is controllably configured for partial or complete removal of the red tissue structures from the product. By means of the actuator, the position of the cutting device is configured adjustably by means of the control device, so that the red tissue structures are removed fully automatically and ideally without manual reworking.

According to a further preferred embodiment of the invention, the cutting device is designed and adapted height-adjustably such that the immersion depth of the cutting device in the product is configured variably for partial or complete removal of the red tissue structures from the product. By means of the variably configured immersion depth, i.e. a measure of how far for example a cutting edge of the cutting device penetrates into the product, the height profile of the product on removal of the red tissue structure is taken into account so complete separation or partial removal of the red tissue structures from the remaining product takes place with great precision.

The present object is also achieved by a method of the type cited hereinbefore, wherein the method comprises the steps of continuous transport of the products through an inspection area in a conveying direction, illumination of the product with a flat light field of a light source to form a light line running transversely to the conveying direction of the product, recording of the portions of light reflected by the product by means of an optical sensor means of a detecting device, wherein the light source is configured as an infrared light source and the plane of the flat light field relative to the conveying direction is tilted by a light field angle of less than 90°. The method according to the invention, as already explained above in detail in connection with the apparatus according to the invention, offers the advantage of a reliable and precise identification of red tissue structures in the products.

According to a preferred embodiment of the invention, the portions of light reflected by the product are recorded at a viewing angle of less than 90° relative to the conveying direction. This offers the advantage that the light line running transversely to the conveying direction on the product is not partially shadowed by surface unevenness of the product. Thus the light line is detected by a detecting device without gaps or interruptions, and largely independently of the unevenness of the product surface.

A further advantageous embodiment of the invention is distinguished in that the light field angle is greater than the viewing angle. This offers the advantage that the reflected portions of light recorded by the detecting device at the viewing angle cannot be shadowed or concealed by unevenness on the surface of the product, so that the reflected portions of light can in any case reach the detecting device unobstructed.

A further expedient embodiment of the invention is characterised in that a plurality of individual images is recorded by means of the detecting device for each of the products. By recording individual images of the product or the light line on the product, the course of the contour of the product is detected so the position of the red tissue structures is determined over the entire product length.

A further expedient embodiment of the invention is characterised in that on the basis of the individual images, by means of an analysis means, border lines are detected between the areas of the red tissue structures and the other product areas of the product.

According to a further advantageous embodiment of the invention, lines of the same light intensity are determined in the individual images in order for the border lines to be determined by means of the analysis means. The respective advantages have already been described in connection with the apparatus according to the invention, so that to avoid repetition, reference is made to the corresponding passages of the description.

BRIEF DESCRIPTION OF THE DRAWINGS

Further preferred and/or expedient features and embodiments of the invention arise from the sub-claims and the description. Particularly preferred embodiments are explained in more detail with reference to the enclosed drawings. The drawings show:

DETAILED DESCRIPTION OF EMBODIMENTS

Figure 1:
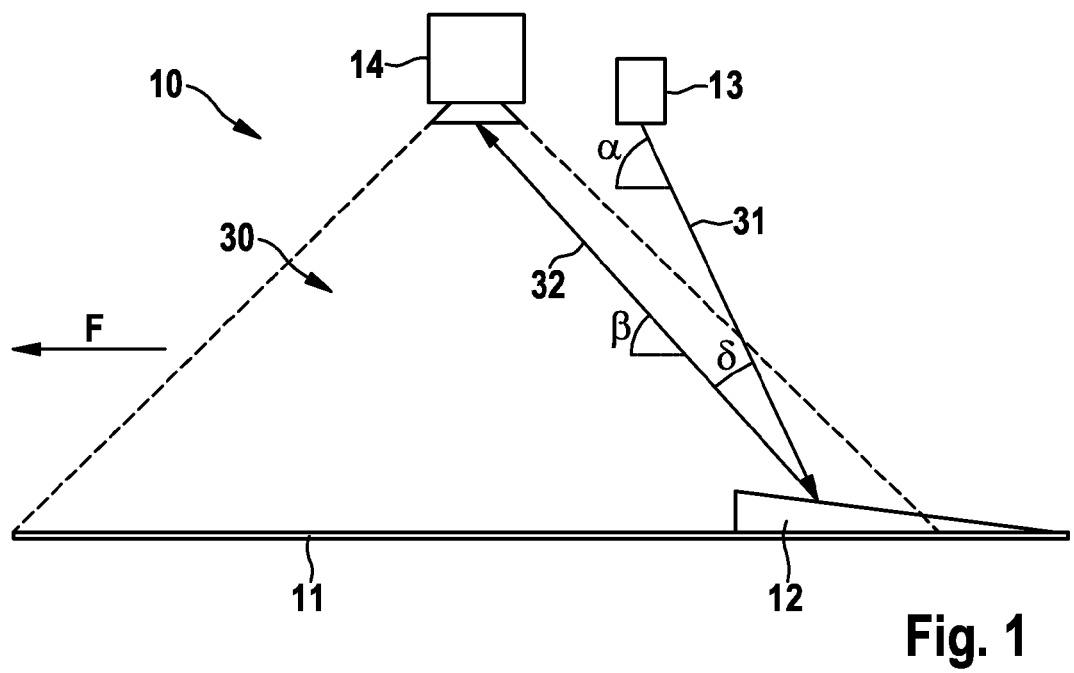
FIG. 1 a diagrammatic depiction of a first embodiment of the apparatus according to the invention in side view, FIG. 2 a diagrammatic depiction of a cross section of a tuna fish, FIG. 3 a diagrammatic depiction of a tuna fish fillet including part of a conveying device in perspective view, and FIG. 4 a diagrammatic depiction of the tuna fish fillet shown in FIG. 3 and part of the conveying device in cross section.

FIG. 1 shows a diagrammatic depiction of a first embodiment of the apparatus 10 according to the invention in a side view. The apparatus 10 comprises a conveying device 11 by means of which the products 12 are transported continuously in a conveying direction F. For example the conveying device 11 is formed as an endless conveyor. The products 12 are preferably parts of slaughtered animal bodies, for example fish, meat or poultry parts. Particularly preferably, the products 12 are tuna fish fillets.

The apparatus 10 furthermore comprises a light source 13. The light source 13 is adapted and designed such that it emits a flat light field 31, wherein the flat light field 31 forms a light line running transversely to the conveying direction F. In other words, the light source 13 is designed and adapted to form a light line on the product 12 which runs transversely to the conveying direction F.

The apparatus 10 furthermore comprises a detecting device 14 with an optical sensor means. Alternatively, the detecting device 14 comprises a plurality of sensor means. The optical sensor means is designed and adapted to receive the portions of light 32 reflected by the product 12. The optical sensor means is for example configured as a CCD camera or CCD line camera. Preferably, the light source 13 is an infrared light source. Particularly preferably, the light source 13 is configured to emit light in the infrared wavelength range. Alternatively, the light source 13 covers a wavelength range starting from the infrared range through to visible red.

The light source 13 is arranged such that the plane of the flat light field 31 relative to the conveying direction F is tilted by a light field angle α of less than 90°. In other words, the plane is preferably not orthogonal to the conveying direction F, so that the plane of the flat light field 31 does not hit the surface of the product 12 vertically but is tilted by a corresponding angular degree. The oblique position of the flat light field 31 leads to a distortion of the light lines on the product 12 depending on the geometry of the product 12, so that the form and geometry of the product 12 can be concluded from the course of the light lines.

Preferably, the optical sensor means of the detecting device 14 is designed and adapted to record images of the light lines running according to the geometry of the product 12, and adapted to the respective wavelengths of the light emitted by the light source 13.

Alternatively, the detecting device 14 may comprise further optical sensors which are configured and designed to record images or image data in another wavelength range, for example the visible range. The detecting device 14 in this case is configured to process the signals from several of the optical sensors. For example, the detecting device 14 comprises processing means for superimposing the recorded images of several of the optical sensors.

Furthermore, in addition to the light source 13, a further light source (not shown in the drawing) is arranged to illuminate the product 12 with light of visible wavelength. Whereas the detecting device 14 comprises the optical sensor means for receiving images of the product 12 and the light lines running thereon in the infrared range, in addition a further optical sensor means (not shown in the drawing) is arranged to receive images of the product 12 in the visible light wavelength range. Particularly preferably, the optical sensor means and further optical sensor means are formed as an integral sensor means, i.e. combined in one sensor means. For example, this one sensor means is configured as a camera which is sensitive to both the infrared and the visible light wavelength range. In other words, the detecting device 14 preferably comprises only one sensor means which is designed and adapted to record images in both the infrared and the visible light wavelength range. As described above, the detecting device 14 is preferably adapted to determine, by means of the processing means, by combination of the recorded images in the visible and infrared light wavelength range, additional information on the composition, in particular the geometry of the products 12. For example, in this way it is possible to determine geometric data of the product 12, such as the product width or product contour.

Figure 2:
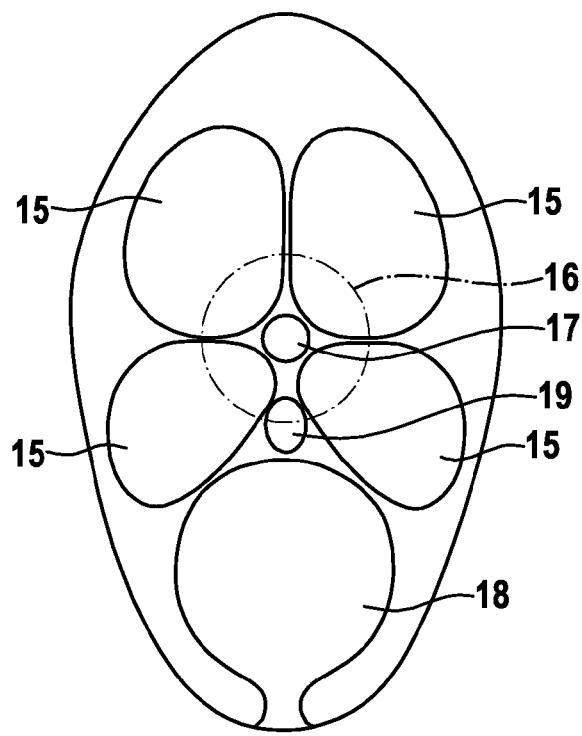

With reference to FIG. 2, which shows a diagrammatic depiction of a cross section of a tuna fish, the function of the apparatus according to the invention for non-contact identifying of red tissue structures 16 will be explained as an example. The red tissue structures 16 shown in FIG. 2 are red muscle flesh. The present invention is not however restricted to the identification of red muscle flesh 16 in tuna fish but is also suitable in principle for other products 12, i.e. for example fillets or flesh parts of other animals.

The highly diagrammatic cross section of a tuna fish shown in FIG. 2 shows the muscle strands 15 which surround the heavily blooded red tissue structures 16 of red muscle flesh. The red tissue structures 16 in turn surround the backbone 17. A large blood vessel 19 is arranged between the backbone 17 and the belly cavity 18, which is responsible amongst others for the heavy blood circulation of the red muscle flesh. The muscle strands 15 and red muscle flesh are translucent tissues. The muscle strands 15 and the red tissue structures 16 with the red muscle flesh have different opacities, i.e. each has a different light transmission capacity. Because of the different opacities, the light line on the surface of the product 12 appears with different widths. The detecting device 14 is designed and adapted to analyse the images recorded by the optical sensor in that, in particular, the width of the light lines is evaluated in order to identify the red muscle flesh. Preferably, the light source 13 and the optical sensor means are arranged spaced apart, i.e. the light source 13 and the optical sensor means are arranged at a distance from each other relative to the conveying direction F in order for example to determine the height contour of the product 12.

Further preferably, the detecting device 14 as shown in FIG. 1 is arranged such that the portions of light 32 reflected by the product 12 are recorded at a viewing angle β of less than 90° to the conveying direction F. The viewing angle β here designates the angle between the conveying direction F and the reflected portions of light 32. In other words, the light source 13 and the detecting device 14 are arranged such that both the illumination of the product 12 by means of the flat light field 31 and the recording of the portions of light 32 reflected by the product 12 take place at an oblique angle.

Advantageously, the light source 13 and the detecting device 14 are furthermore arranged such that the light field angle α is greater than the viewing angle β. The angular difference δ between the light field angle α and the viewing angle β designates the angle between the flat light field 31 falling on the product 12 and the reflected portions of light 32.

Preferably, the detecting device 14 is arranged downstream of the light source 13 in the conveying direction F. In other words, the detecting device 14 and the light source 13 are arranged such that the products 12 are illuminated at an oblique angle against the conveying direction F, and the reflected portions of light 32 have at least a partial component which also points in the conveying direction F.

Further preferably, the light source 13 is configured as a linear laser. Preferably, linear lasers with a power of 5 to 500 mW are used. Alternatively, the light source 13 is a conventional light source with a correspondingly strong light beam and adapted lens to generate the flat light field 31 described above and the light line running on the product 12.

Particularly preferably, the light source 13 has a wavelength between 600 nm and 1200nm, i.e. a wavelength range which extends from the visible red through to the infrared range. Further preferably, the light source 13 has a wavelength in the range between 650 nm and 900 nm and is thus optimally adapted to the absorption properties of heavily blooded tissues such as the red tissue structures 16.

Advantageously, the detecting device 14 is designed and adapted to record a plurality of individual images of the product 12. In other words, the detecting device 14 is configured such that several individual images of the product 12 are recorded which depict a plurality of segments of the continuously transported product 12.

Further preferably, the detecting device 14 comprises an analysis means which is designed and adapted to analyse the individual images recorded. For this the analysis means is furthermore designed and adapted to determine border lines between the areas of red tissue structures 16, in particular the red muscle flesh, and the other product regions 33, for example the muscle strands 15, on the basis of the individual images.

Preferably, the analysis means is designed and adapted to detect lines of the same light intensity in the individual images in order to determine the border lines. The border lines define the transition between the red tissue structures 16 and the other tissue parts, in particular the muscle strands 15.

Figure 3:
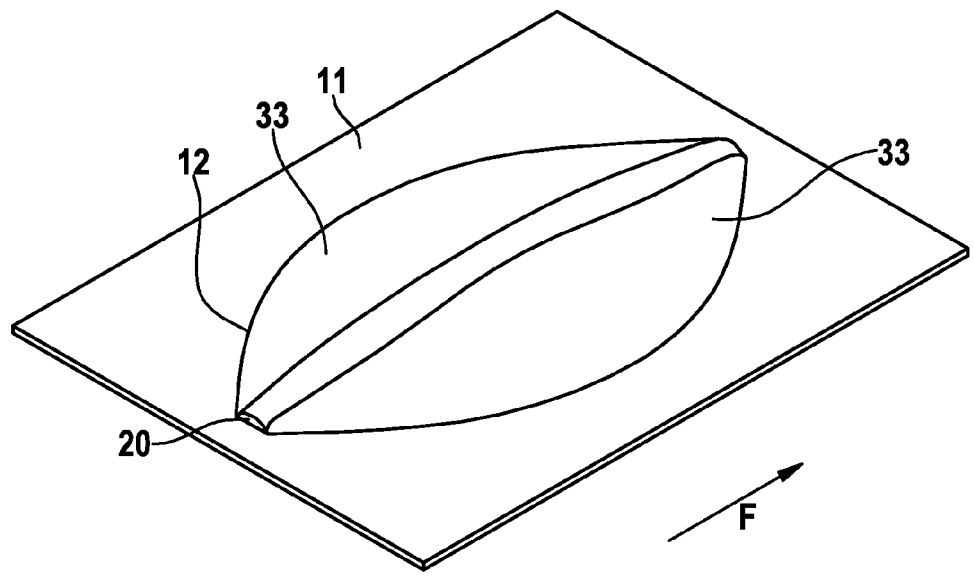

FIG. 3 shows diagrammatically a tuna fish fillet including part of the conveying device 11 in perspective view. The above-mentioned region of red tissue structures 16 can be seen as a strip 20 of red muscle meat in FIG. 3. The product 12, for example a tuna fish fillet, is oriented along the backbone 17 in the conveying direction F and is transported continuously by means of the conveying device 11, indicated merely diagrammatically in FIG. 3.

Advantageously, the present invention also comprises an arrangement for removing the strip 20 of red tissue structure 16 from the product 12. The arrangement comprises the apparatus described above for non-contact identifying of red tissue structures 16 in the product 12 or products 12. Furthermore, the arrangement comprises a cutting device 21 (not shown in the figures). The cutting device 21 is designed and adapted for partial or complete removal of the strip 20 of red tissue structure 16 from the product 12. The cutting device 21 is controlled by means of a control device (not shown in the figures). The control device controls the cutting device 21 such that the area determined by means of the apparatus according to the invention for non-contact identifying of red tissue structures 16, in particular the strips 20, is removed completely or partially from the products 12. The cutting device is optionally configured such that either the strip 20 is completely removed from the product 12 or only partially removed, in that the strip 20 is removed in part areas by cutting or puncturing the product 12, but after cutting remains connected to the product 12 in order for example to be removed definitively from the product 12 by manual processing.

Preferably, the cutting device 21 is configured moveably relative to the product 12 so that the distance—in particular the vertical distance—between the product 12 and the cutting device 21 is configured variably. Particularly preferably, the cutting device 21 comprises at least one actuator (not shown in the drawing). By means of the actuator, the cutting device 21 is configured controllably i.e. the position of the cutting device 21 is configured changeably relative to the product 12 or relative to the conveying device 11. By means of the control device, the position of the cutting device is controlled such that the red tissue structures or the strip 20 are/is removed partly or completely from the product 12.

Advantageously, the cutting device 21 is configured variably in height, i.e. the distance between the respective cutting edge and the product 12. In this way, the immersion depth of the cutting device 21 in the product 12 is configured variably for partial or complete removal of the red tissue structures 16 or strip 20.

Figure 4:
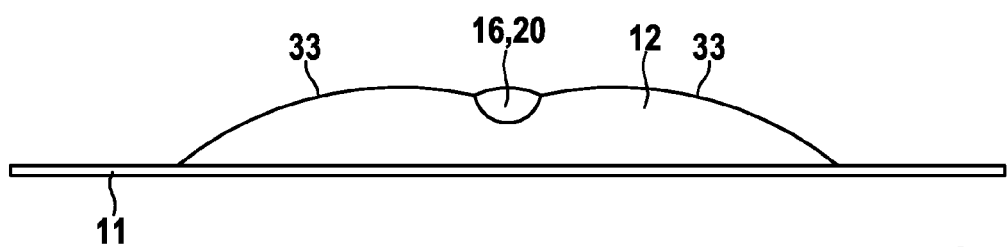

FIG. 4 shows a diagrammatic depiction of the tuna fish fillet shown in FIG. 3 and part of the conveying device 11 in cross section. The conveying direction F points into the drawing plane in FIG. 4. In the middle, the area of red tissue structures 16 of the red muscle flesh can be seen in the form of the strip 20 which is bordered on both sides by the other product areas 33.

The present invention also comprises a method for non-contact identifying of red tissue structures 16 in products 12 of slaughtered animal bodies. To avoid repetition, in connection with the method according to the invention, reference is made in full to the statements above relating to the apparatus 10 according to the invention and the arrangement according to the invention. The statements made in connection with the apparatus 10 and the arrangement apply correspondingly to the method according to the invention. To clarify the sequence of the method according to the invention, selected aspects of the method are described additionally below.

The method of the type cited hereinbefore comprises the following steps. The products 12 are transported continuously through an inspection area 30 in the conveying direction F. The inspection area 30 is formed by the light source 13 shown in FIG. 1 and the detecting device 14. The inspection area 30 comprises the detection region of the detecting device 14 delimited by the dotted lines in FIG. 1. By means of the light source 13, the products 12 are illuminated with a flat light field 31, wherein the light source 13 or the flat light field 31 emitted thereby is configured to form a light line running transversely to the conveying direction F. The portions of light 32 reflected by the product 12 are recorded by means of the optical sensor means of the detecting device 14. Reflected portions of light 32 designate both portions of light 32 reflected directly at the product surface, but in particular the portions of light which penetrate into the deeper layers of the product 12 and are scattered there. The light source 13 illuminates the products 12 and is configured as an infrared light source. Furthermore, the plane of the flat light field relative to the conveying device 11 is tilted by a light field angle α of less than 90°.

The invention claimed is:

1. Apparatus for non-contact identifying of red tissue structures in products of slaughtered animal bodies, comprising a conveying device for continuous conveyance of the products in a conveying direction, a light source configured to generate a flat light field which is designed and adapted to form a light line running transversely to the conveying direction of the product from the flat light field, a detecting device for identifying the red tissue structures which comprises at least one optical sensor means for recording the portions of light reflected by the product, wherein the light source is configured as an infrared light source and the light source is arranged such that the plane of the flat light field is tilted relative to the conveying direction by a light field angle of less than 90°, wherein the light source and the optical sensor means are arranged spaced apart in the conveying direction, and the detecting device is arranged such that the light portions reflected by the product are recorded at a viewing angle of less than 90° relative to the conveying direction, and the light source and detecting device are arranged such that the light field angle is greater than the viewing angle.

2. Apparatus according to claim 1, characterised in that the detecting device is arranged downstream of the light source in the conveying direction.

3. Apparatus according to claim 1, characterised in that the light source is designed as a linear laser.

4. Apparatus according claim 1, characterised in that the light source has a wavelength between 600 nm and 1200 nm.

5. Apparatus according to claim 1, characterised in that the detecting device is designed and adapted to record a plurality of individual images.

6. Apparatus according to claim 5, characterised in that the detecting device comprises an analysis means which is designed and adapted to determine border lines between areas of the red tissue structures and the other product areas of the product on the basis of the individual images.

7. Apparatus according to claim 6, characterised in that the analysis means is designed and adapted to detect lines of the same light intensity in the individual images in order to determine the border lines.

8. Arrangement for removing a strip of red tissue structures from products of slaughtered animal bodies, comprising an apparatus for non-contact identifying of red tissue structures in the products, a cutting device for partial or complete removal of the red tissue structures from the products, a control device adapted and designed to control the cutting device along the regions determined by the apparatus for non-contact identifying of red tissue structures, wherein the apparatus for non-contact identifying of red tissue structures in the products is designed according to claim 1.

9. Arrangement according to claim 8, characterised in that the cutting device is designed moveably relative to the product.

10. Arrangement according to claim 9, characterised in that the cutting device comprises at least one actuator, by which the cutting device is adapted controllably for partial or complete removal of the red tissue structures from the product.

11. Arrangement according to claim 8, characterised in that the cutting device is designed and adapted height-adjustably so that the immersion depth of the cutting device in the product is designed variably for partial or complete removal of the red tissue structures from the product.

12. Method for non-contact identifying of red tissue structures in products of slaughtered animal bodies, comprising the steps:

continuous transport of the products through an inspection area in a conveying direction, illumination of the products by a flat light field of a light source to form a light line running transversely to the conveying direction of the product, recording of the portions of light reflected by the products by an optical sensor means of a detecting device, wherein the light source is designed as an infrared light source and the plane of the flat light field relative to the conveying direction is tilted by a light field angle of less than 90°, and the portions of light reflected by the product are recorded at a viewing angle ($\beta$) of less than 90° relative to the conveying direction, wherein the light field angle is greater than the viewing angle.

13. Method according to claim 12, characterised in that a plurality individual images is recorded by the detecting device of each of the products.

14. Method according to claim 13, characterised in that, on the basis of the individual images, by an analysis means, border lines are determined between areas of red tissue structures and the other product areas of the product.

15. Method according to claim 14, characterised in that lines of the same light intensity are determined in the individual images for the determination of the border lines by means of the analysis means.

\* \* \* \* \*